United States Patent [19]

Minami

[11] Patent Number: 5,749,827
[45] Date of Patent: May 12, 1998

[54] OBJECTIVE OPTICAL MEMBER WITH AIR GAP FOR ENDOSCOPE IMAGING UNIT

[75] Inventor: Itsuji Minami, Omiya, Japan

[73] Assignee: Fuji Photo Optical Co., Ltd., Omiya, Japan

[21] Appl. No.: 607,351

[22] Filed: Feb. 26, 1996

[30] Foreign Application Priority Data

Mar. 7, 1995 [JP] Japan .................................. 7-074588

[51] Int. Cl.⁶ .................................................. A61B 1/04
[52] U.S. Cl. ........................... 600/109; 348/340; 348/65
[58] Field of Search ..................................... 600/109, 129, 600/130; 348/65, 340, 338; 359/619, 367

[56] References Cited

U.S. PATENT DOCUMENTS

| | | | |
|---|---|---|---|
| 4,682,219 | 7/1987 | Arakawa | 348/65 |
| 4,867,137 | 9/1989 | Takahashi | 600/109 |
| 4,868,644 | 9/1989 | Yabe et al. | 600/109 |
| 5,153,734 | 10/1992 | Kanamori et al. | 348/340 |
| 5,239,412 | 8/1993 | Naka et al. | 359/619 |
| 5,430,475 | 7/1995 | Goto et al. | 348/65 |

*Primary Examiner*—John P. Leubecker
*Attorney, Agent, or Firm*—Ronald R. Snider

[57] ABSTRACT

An assembled body of an electronic endoscope which is capable of reducing the diameter of the endoscope and simplifying the structure thereof. The assembled body comprises an imaging device with a color filter and a microlens provided on the imaging plane, and an objective optical member for catching an object of inspection. An opening is formed in a cover glass as the objective optical member, and the cover glass is directly adhered to the imaging plane of the imaging device. An air gap is set by the opening of the cover glass. The cover glass and the imaging device are adhered to each other with an adhesive so as to keep the air gap in an airtight state. It is thus possible to directly combine the imaging device with the optical member without using a package. A groove may be formed as the air gap in a prism as a part of the objective optical member.

4 Claims, 5 Drawing Sheets

FIG.5(A) FIG.5(B)
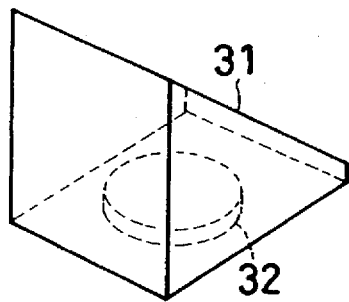 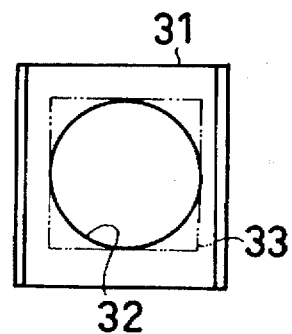
FIG.6(A) FIG.6(B)
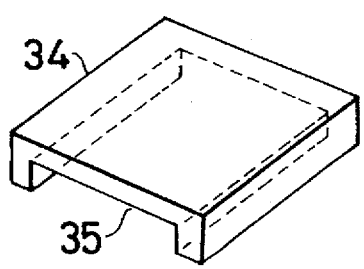 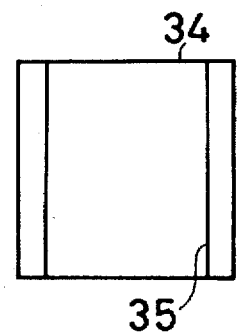

5,749,827

OBJECTIVE OPTICAL MEMBER WITH AIR GAP FOR ENDOSCOPE IMAGING UNIT

BACKGROUND OF THE INVENTION

This application claims the priority of Japanese Patent Application No. 7-74588 filed on Mar. 7, 1995.

1. Field of the Invention

The present invention relates to a structure of an assembled body which is provided in an imaging portion of an electronic endoscope and which incorporates an imaging device having a color filter and a microlens.

2. Description of the Related Art

FIG. 7 is a side elevational view of an assembled body which is provided at the end portion of an electronic endoscope and which incorporates an imaging device. In the structure shown in FIG. 7, an objective portion 2 having an observation window 1 is connected to a cover glass 4 via a prism 3, and the cover glass 4 is disposed at the position which enables the cover glass 4 to close the opening in the upper surface of a package 5. A charged coupled device (CCD) 6 is disposed within the package 5, and the package 5 is mounted on a circuit board 7. Therefore, the CCD 6 is also electrically connected to the circuit board 7 via the package 5.

The CCD 6 is used in a simultaneous (not field sequential) image pickup apparatus and it is, for example, an interline CCD. A color filter and a microlens (not shown) are provided on the imaging plane on the upper surface of the CCD 6. The color filter is provided so as to obtain a color image using, for example, a complementary color mosaic, while the microlens is provided so as to increase the light incidence efficiency with respect to the photosensor of the CCD 6. The CCD 6 provided with the color filter is attached to the interior of the package 5 in an airtight state (the package 5 may be filled with degeneration preventive gas) so as to prevent the color of the color filter from changing.

FIG. 8 shows the interior of the end portion of the endoscope seen from the front side. The assembled body including the objective lens portion 2, the prism 3, the cover glass 4, the package 5, the CCD 6 and the circuit board 7 is disposed on the upper side of the end portion 8. Irradiation windows 9A, 9B to which a light guide is connected are disposed on both sides of the observation window 1 of the objective portion 2 in the vicinity thereof, and a tool insertion channel 10 for guiding a tool such as forceps is provided on the underside of the circuit board 7. According to this structure, when light is projected into the body as the object of inspection through the irradiation windows 9A, 9B, the image of the internal body is caught by the CCD 6 via the observation window 1.

The great problems confronting a conventional endoscope are how to reduce the diameter of the end portion and how to simplify the structure of the endoscope. Especially, reduction in the diameter of the end portion of an endoscope for the bronchi is in strong demand. In order to meet this demand, attention is paid to the assembled body of an imaging device in the present invention. As shown in FIG. 8, the cover glass 4, the package 5 and the circuit board 7 occupy the length of T1 in the diametrical direction of the end portion 8, T1 being equivalent to the sum of the thicknesses of these elements 4, 5 and 7. In other words, if the thickness T1 is reduced, it is possible to reduce the diameter of the end portion 8.

SUMMARY OF THE INVENTION

Accordingly, it is an object of the present invention to eliminate the above-described problems in the related art and to provide an assembled body of an imaging device in an endoscope which is capable of reducing the diameter of the end portion of the endoscope and simplifying the inner structure of the endoscope.

To achieve this end, an assembled body of an imaging device in an electronic endoscope according to the present invention comprises: an imaging device with a color filter provided on the imaging plane; and an objective optical member which is in contact with the color filter of the imaging device so as to catch an object of inspection, and which is provided with an air gap corresponding to an imaging range.

A microlens may be provided on the color filter of the imaging device.

It is possible to provide a plate member having an opening or a groove (concave space) as the air gap and dispose the plate member in contact with the imaging plane. Alternatively, it is possible to provide a prism with a groove formed and dispose the prism in contact with the imaging plane as the objective optical member.

It is preferable to adhere the elements with each other with an adhesive so as to keep the air gap in an airtight state.

According to this structure, for example, a color filter is provided on the surface of an imaging device, and a microlens is provided on the color filter. A flat glass plate having an opening is directly adhered to the microlens with an adhesive. An objective optical member is adhered to the glass plate with an adhesive so as to keep, for example, the opening in an airtight state. In such an assembled body of an imaging device, the opening formed in the glass plate serves as the air gap which is provided in the upper portion of a conventional package. Therefore, if it is assumed that the glass plate and the cover glass of the package have the same thickness, the length in the diametrical direction of the assembled body of the present invention is shortened by the length corresponding to the air gap in the conventional package.

The above and other objects, features and advantages of the present invention will become clear from the following description of the preferred embodiments thereof, taken in conjunction with the accompanying drawings.

BRIEF DESCRIPTION OF THE DRAWINGS

FIG. 5(A) is a perspective view of a prism in a third embodiment of the present invention;

FIG. 5(B) is a bottom view of the prism shown in FIG. 5(A);

FIG. 6(A) is a perspective view of the glass plate in a fourth embodiment of the present invention;

FIG. 6(B) is a bottom view of the glass plate shown in FIG. 6(A);

DESCRIPTION OF THE PREFERRED EMBODIMENTS

Figure 1:
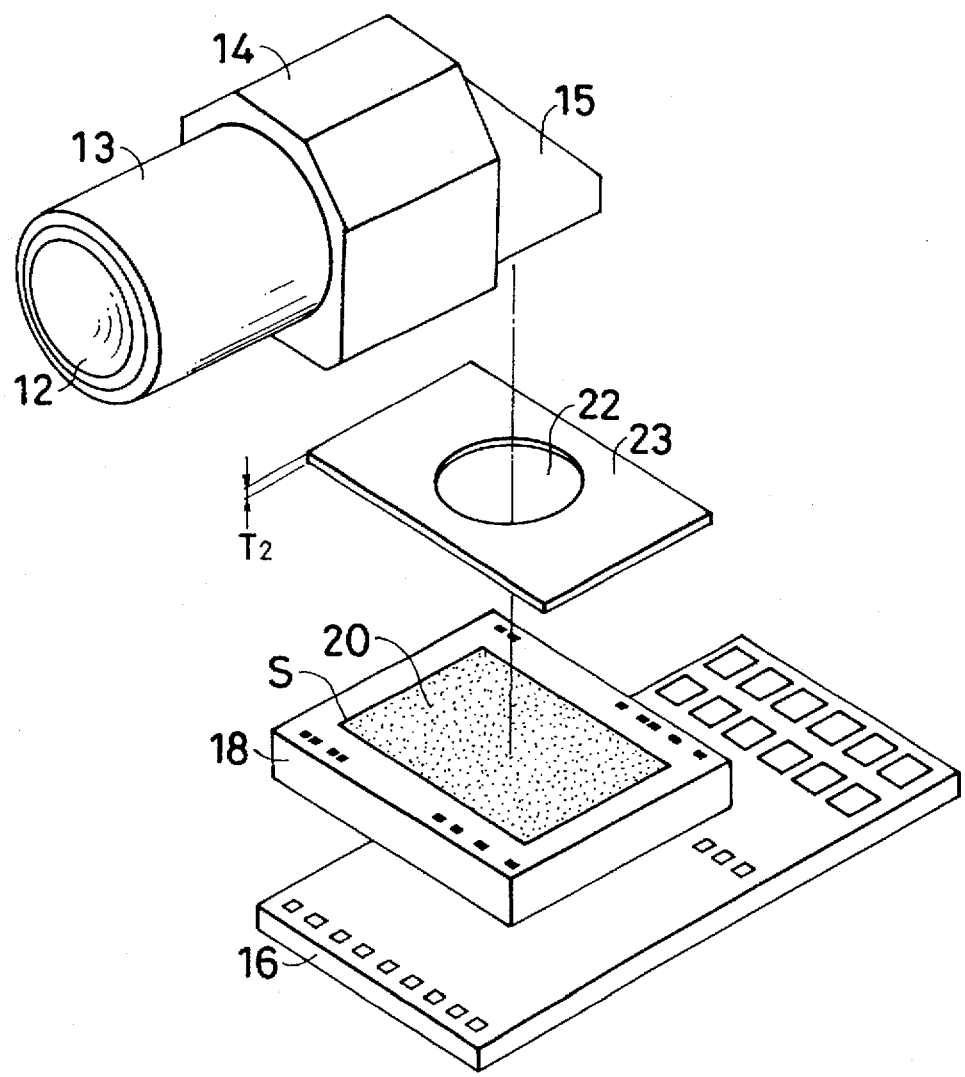
FIG. 1 is an exploded perspective view of a first embodiment of an assembled body of an imaging device in an electronic endoscope according to the present invention.
Figure 2:
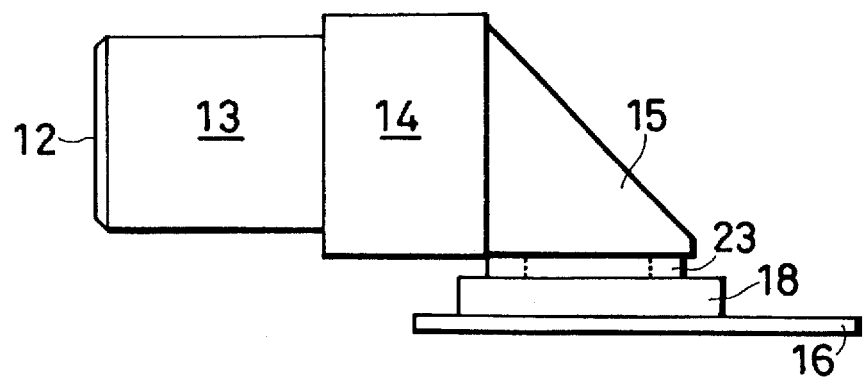
FIG. 2 shows the assembled body shown in FIG. 1 in the assembled state.
Figure 3:
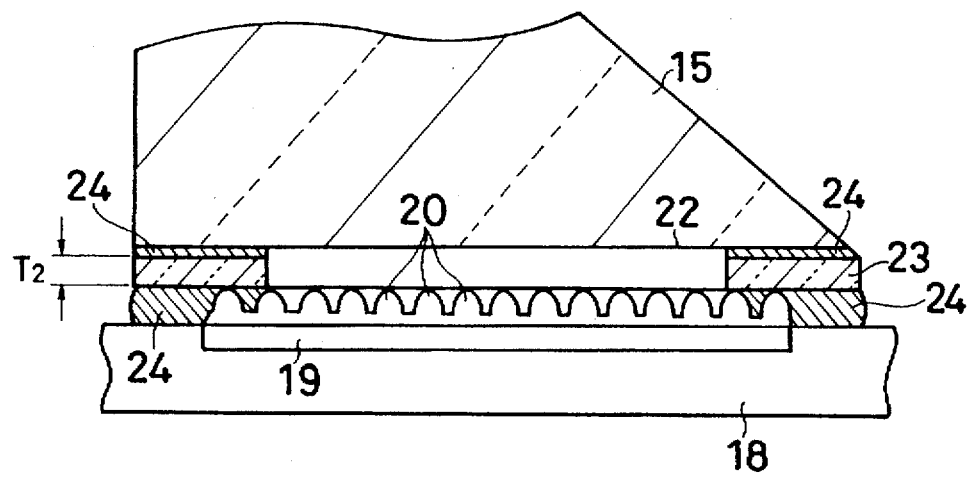
FIG. 3 is an explanatory view of the structure of the connecting portion between the CCD and the glass plate in the first embodiment.

FIG. 1 is an exploded perspective view of a first embodiment of an assembled body of an imaging device in an (simultaneous) electronic endoscope according to the present invention, FIG. 2 shows the assembled body in the assembled state, and FIG. 3 shows the connecting portion between the imaging device and the glass plate. The elements shown in FIG. 1 are disposed at the end portion of an endoscope. An objective portion 13 having an observation window 12 is connected to a housing 14 accommodating an optical filter and the like, and a prism 15. A CCD driving circuit and the like are disposed on the underside of a circuit board 16, and a CCD 18 as an imaging device is attached to the upper surface of the circuit board 16 and connected to predetermined terminals. A color filter 19 is provided on the imaging plane on the upper surface of the CCD 18, as shown in FIG. 3, and a microlens 20 (schematically enlarged in FIG. 3) is provided on the color filter 19.

A glass plate (flat plate) 23 having a thickness of T2 (e.g., about 0.1 mm) with a circular opening (through hole) 22 formed therein is inserted between the CCD 18 and the prism 15. As shown in FIG. 1, the glass plate 23 is disposed so that the opening 22 is positioned at the central portion of the imaging range S of the CCD 18, and the glass plate 23 is directly adhered to the microlens 20 with an adhesive 24, as shown in FIG. 3. Similarly, the prism 15 is adhered to the glass plate 23. The elements shown in FIG. 1 are assembled in this manner, so that the assembled body shown in FIG. 2 is obtained. The opening 22 is filled with predetermined color filter degeneration preventive gas, thereby keeping the opening 22 in an airtight state. The area defined by the circular opening 22 is an actual imaging range, and an image obtained is the part of the object of inspection caught in this range.

Figure 7:
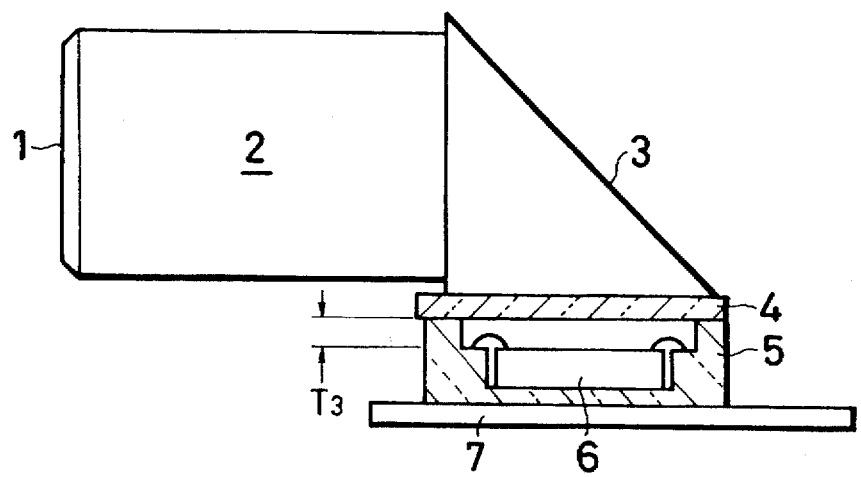
FIG. 7 shows the structure of a conventional assembled body of an imaging device.
Figure 8:
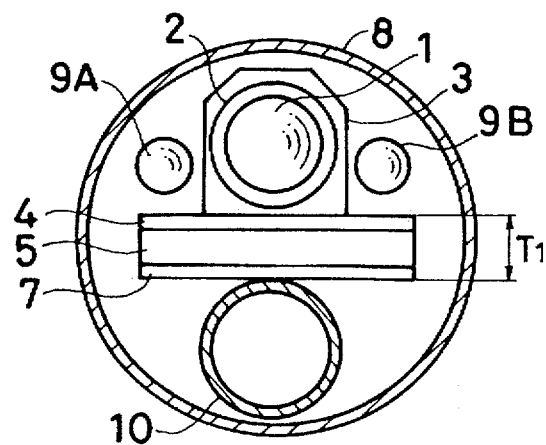
FIG. 8 is a front view of the interior of an endoscope using a conventional assembled body.

According to this embodiment, the space having a length of T2 which is formed by the opening 22 of the plate glass 23 serves as an air gap between the CCD 18 (microlens 20) and the prism 15, which obviates the air gap T3 in the package 5 shown in FIG. 7. It is therefore possible in this embodiment to shorten the length in the diametrical direction (in the vertical direction in the drawings) of the endoscope at least by the length which corresponds to the air gap T3, thereby contributing to the reduction in the diameter of the endoscope.

Owing to the existence of the airtight space in the opening of the glass plate 23, it it possible to prevent the color of the color filter 19 from changing due to degeneration or the like, and since light from the objective portion 2 does not pass through the cover glass 4, it is possible to enhance the light collecting efficiency of the microlens 20.

Figure 4:
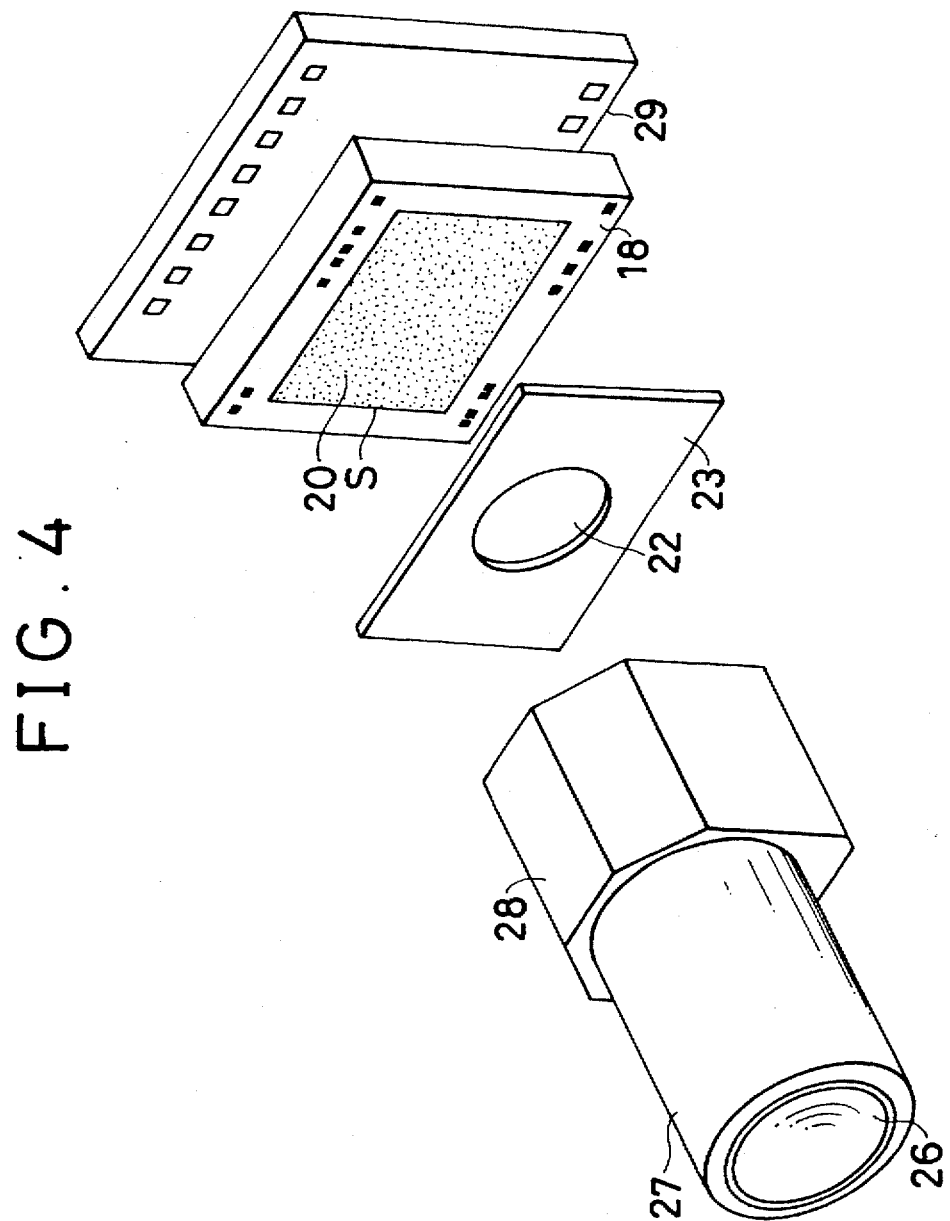
FIG. 4 is an exploded perspective view of a second embodiment of an assembled body of an imaging device in an electronic endoscope according to the present invention.

FIG. 4 shows the structure of a second embodiment of the present invention. This embodiment is not provided with a prism. As shown in FIG. 4, an objective portion 27 having an observation window 26, and an optical member 28 having an optical filter or the like are provided. The CCD 18 as an imaging device is disposed vertically with respect to the optical axis of the objective portion 27. A circuit board 29 connected to predetermined terminals is attached to the CCD 18. The glass plate 23 with the opening 22 formed therein is inserted between the CCD 18 and the optical member 28. The glass plate 23 is connected in the same way as in the first embodiment so as to keep the opening 22 in an airtight state.

According to the second embodiment of an assembled body, it is possible to shorten the length in the diametrical direction of the endoscope by the length which corresponds to the air gap T3 in the package 5 shown in FIG. 7. Therefore, if the second embodiment is used for a side-looking type endoscope, it is possible to reduce the diameter of the endoscope.

In the first and second embodiments, the glass plate 23 of about 0.1 mm thick having the opening 22 is used, but another plate member is also usable. For example, a ceramic plate, a rigid plastic plate and another insulating thin film member are usable. The size and the shape of the glass plate 23 and the opening 22 can be freely set within the imaging range S of the CCD 18.

FIG. 5 shows the structure of a third embodiment of the present invention. In this embodiment, an air gap is formed in the prism in the first embodiment. As shown in FIG. 5, a circular groove (concave space) 32 having a depth the same as the thickness T2 is formed in the undersurface of a prism 31, and the prism 31 is used in place of the prism 15 shown in FIG. 1. As compared with the first embodiment, the third embodiment can dispense with the glass plate 23, so that the length of the assembled body in the diametrical direction of the endoscope can be further shortened. It is also possible to form a rectangular groove 33 having the same depth in the prism 31, as shown in FIG. 5(B).

FIG. 6 shows the structure of a fourth embodiment of the present invention. In this embodiment, a groove is formed in the glass plate used in the first and second embodiments. As shown in FIG. 6, a square groove 35 is formed in a glass plate 34 with two sides left as supporting portions. The glass plate 34 is used in place of the glass plate 23 in the first and second embodiments. The square groove 35 in the glass plate 34 serves as an air gap which is disposed on the upper surface an imaging device as shown when FIG. 6 (A) is combined with FIG. 3.

Although both color filter 19 and microlens 20 are provided on the CCD 18 in each embodiment, the present invention is also applicable to an imaging device which is provided only with either a color filter or a microlens. The optical member in which an air gap is formed is not restricted to the glass plate 23 or 34, and an optical filter such as infrared ray insulating filter may also be used.

As explained above, according to the present invention, since an air gap portion is formed in correspondence with the imaging range on the imaging device side of an objective optical member which is in contact with the imaging plane of the imaging device by directly inserting a plate member having an opening, for example, the length in the diametrical direction of an endoscope is shortened, thereby reducing the diameter of the endoscope. In addition, the cover glass is obviated, thereby simplifying the structure of the assembled body.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. An endoscope imaging unit comprising:
   an imaging device with a color filter provided on an imaging plane thereof; and
   an objective optical member which is in contact with said color filter of said imaging device, and which is provided with an air gap corresponding to said imaging plane and wherein said air gap separates said imaging device and said objective optical member; and wherein said objective optical member has a prism which is provided with a groove as said air gap, and which is disposed on an upper surface of said imaging device.

2. An endoscope imaging unit according to claim 1, wherein said imaging device and said objective optical member are adhered to each other with an adhesive so as to keep said air gap in an airtight state.

3. An endoscope imaging unit according to claim 1, wherein said imaging device includes a microlens which is adjacent to said color filter.

4. An endoscope imaging unit comprising:

an imaging device having an imaging plane with a color filter provided on the imaging plane thereof;

an objective optical member having a prism, said prism having a groove for providing an air gap between said imaging device and said objective optical member; and wherein said prism is directly adhered to said imaging device so as to keep said air gap in an airtight state.

* * * * *